US007604830B2

United States Patent
Case et al.

(10) Patent No.: US 7,604,830 B2
(45) Date of Patent: Oct. 20, 2009

(54) METHOD AND APPARATUS FOR COATING INTERIOR SURFACES OF MEDICAL DEVICES

(75) Inventors: Brian C. Case, Bloomington, IN (US); Darin G. Schaeffer, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 737 days.

(21) Appl. No.: 11/159,707

(22) Filed: Jun. 23, 2005

(65) Prior Publication Data

US 2005/0288774 A1   Dec. 29, 2005

Related U.S. Application Data

(60) Provisional application No. 60/582,694, filed on Jun. 24, 2004.

(51) Int. Cl.
*B05D 3/06* (2006.01)
*A61M 25/00* (2006.01)
*B05D 7/22* (2006.01)

(52) U.S. Cl. ............... 427/2.1; 427/2.24; 427/2.25; 427/2.28; 427/2.3; 427/230; 427/236; 427/237; 427/553

(58) Field of Classification Search ............ 427/2.1, 427/2.24, 2.25, 2.28, 2.3, 230, 236–238, 427/553; 118/100, 105
See application file for complete search history.

(56) References Cited

U.S. PATENT DOCUMENTS

| | | | |
|---|---|---|---|
| 4,271,208 A | 6/1981 | Itoh et al. | |
| 4,376,143 A | 3/1983 | Lehmann | |
| 5,128,170 A * | 7/1992 | Matsuda et al. | 427/2.24 |
| 5,603,991 A * | 2/1997 | Kupiecki et al. | 427/508 |
| 5,714,360 A | 2/1998 | Swan et al. | |
| 5,763,504 A * | 6/1998 | Matsuda et al. | 522/87 |
| 6,261,320 B1 | 7/2001 | Tam et al. | |
| 6,447,835 B1 * | 9/2002 | Wang et al. | 427/2.24 |
| 6,586,039 B2 * | 7/2003 | Heinz et al. | 427/2.28 |
| 6,706,025 B2 | 3/2004 | Engelson et al. | |
| 6,723,373 B1 | 4/2004 | Narayanan et al. | |
| 6,743,463 B2 | 6/2004 | Weber et al. | |
| 2003/0204239 A1 | 10/2003 | Carlyle et al. | |
| 2003/0204245 A1 | 10/2003 | Brightbill | |
| 2005/0049691 A1 * | 3/2005 | Mericle et al. | 623/1.23 |
| 2005/0196518 A1 * | 9/2005 | Stenzel | 427/2.1 |

* cited by examiner

*Primary Examiner*—Timothy H Meeks
*Assistant Examiner*—Cachet I Sellman
(74) *Attorney, Agent, or Firm*—Brinks Hofer Gilson & Lione (57) ABSTRACT

A coating can be applied to an endolumenal wall of a medical device by positioning an optical fiber within the lumen, providing a photo-activated chemical to contact the endolumenal wall, supplying the optical fiber with radiation capable of activating the chemical within the lumen, and withdrawing the optical fiber from the lumen at a controlled rate while the radiation is being emitted from the optical fiber to activate the chemical in close proximity to the endolumenal wall.

19 Claims, 4 Drawing Sheets

METHOD AND APPARATUS FOR COATING INTERIOR SURFACES OF MEDICAL DEVICES

CROSS-REFERENCE TO RELATED APPLICATIONS

This application is based on and claims all benefits of U.S. Provisional Ser. No. 60/582,694 filed Jun. 24, 2004.

BACKGROUND

1. Technical Field

The present invention relates to medical devices, particularly surgical instruments and prostheses, having elongated and generally opaque wall structures surrounding an elongated lumen such as catheters, introducers, needles, stent frames and stent grafts. The invention particularly relates to methods and apparatus for applying selected coatings to endolumenal surfaces of such devices.

2. General Background

Catheters, introducers, and other similar medical devices having elongated lumens are used to deliver diagnostic and therapeutic agents and appliances to remote locations through the vascular systems within the body of a patient. Needles, stent frames, stent grafts and other similar medical devices have elongated, although, generally, proportionally somewhat shorter lumens that are used to provide a pathway for vital fluids to and through the tissue and vascular systems of the patent. Further, when expanded radially, stent frames have a more or less porous structure rather than the substantially continuous wall character of the other medical devices considered herein.

Considerable attention has been given to controlling the physical interaction between such devices and the various structures and fluids through which the devices are moved by manipulating the surface chemistry of various portions of the devices. For example, U.S. Pat. No. 6,706,025 to Engelson, et al., discloses coating various longitudinal segments of the exterior surface of a catheter with lubricious hydrophilic polymers selected to provide various frictional characteristics to the different longitudinal segments. The selected polymeric coatings are applied by spraying a solution or suspension of the polymers or of oligomers of the monomers onto the catheter, or by dipping the catheter into the solution or suspension after sealing the open ends of the catheter. The coating is allowed to dry. During or after drying, the coating can be irradiated with ultra-violet light or ionizing radiation to promote polymerization and cross-linking of the coating to the exterior surface of the catheter. The coating procedure can optionally be repeated so that one or more additional coatings are applied in a similar manner. No means are disclosed to specifically apply any coating liquids to the endolumenal wall of the catheter. No means are disclosed to provide irradiation to encourage the polymerization of any coating fluids that might accidentally flow into the lumen of the catheter. As a result, the interior surface chemistry of the catheter is essentially totally unaffected by the procedures and chemical agents disclosed in Engelson.

Other processes for coating stent frames are known from including brushing, wiping, pad printing, ink-jet printing, electrostatic liquid spraying, and electrostatic powder coating. The desirability of coating stent frames with a polymer dissolved in a solvent optionally containing a therapeutic substance such as actinomycin D, paclitaxel, docetaxel, or rapamycin is known. Known polymers that can be used to coat stents with such substances include, for example, a number of polymethacrylates, polycaprolactone, and polysilanes. The therapeutic substances can also be anti-neoplastic agents, anti-proliferative agents, anti-inflammatory agents, growth control factors, antibiotics, antioxidants, and combinations thereof.

However, there remains a need for methods and apparatus to apply a desired surface chemistry to the endolumenal walls of catheters, introducers, needles, stent frames, stent grafts, and other similarly structured medical devices, to achieve the recognized benefits of such modifications in surface chemistry. There is a particular need to coat the endolumenal walls or surfaces of stent frames and stent grafts with substances that will effectively inhibit targeted adverse physiological reactions, such as restenosis, caused by uncoated surfaces of medical devices inserted or implanted in a patient's body.

BRIEF SUMMARY

Apparatus for applying a coating to an endolumenal wall of a medical device includes an optical fiber dimensioned to fit within the lumen of the medical device. The optical fiber must be capable of carrying radiation having a suitable wavelength to interact with a chemical agent of the coating material to be applied to the endolumenal wall. The optical fiber must have a first end that is able to be coupled to a source of such radiation. The source of radiation can include intensity controls to govern the amount of radiation to be delivered to the optical fiber first end.

The optical fiber desirably has a second end with a structure conducive to illuminate the endolumenal wall adjacent to the second end of the optical fiber. The optical fiber second end can take the form of a divergent lens that causes radiation passing through the second end to be spread onto that portion of the endolumenal surface that is beyond the optical fiber second end. The optical fiber second end can also take the form of an inwardly protruding conical reflective surface that causes radiation to be reflected outward through the side wall of the optical fiber.

A coating material supply provides at least a monomolecular film of the coating material immediately adjacent to the optical fiber second end. The coating material supply can take the form of a reservoir of the coating material of a size suitable to permit the medical device to be at least partially immersed in the coating material. The coating material supply can also take the form of a pump coupled to a reservoir of the coating material and to the medical device in such a manner as to permit a flow of the coating material to be supplied to and/or through the lumen of the device. The coating material supply can also take the form of a source of the coating material to a capillary space between the optical outer surface and the endolumenal wall, the capillary force being relied upon to distribute the coating material to a position adjacent to the optical fiber second end. A flow of gas can be used to inhibit excessive coating.

The second end of the optical fiber desirably travels at least once through at least the length of any portion of the lumen to which the coating material is to be applied. The second end of the optical fiber can travel through the entire length of the lumen at a controlled rate of speed, which can vary from segment to segment of the lumen. The rate of speed can be related to the amount of optical energy needed to cause a desired reaction of the photo-active component of the coating material. Suitable position and drag sensors can be included to aid in the control of the traveling characteristics of the optical fiber with respect to the lumen.

A coating can be applied to an endolumenal wall of a medical device by positioning an optical fiber within the lumen, providing a photo-activated chemical to contact the endolumenal wall, supplying the optical fiber with radiation capable of activating the chemical within the lumen, and withdrawing the optical fiber from the lumen at a controlled rate while the radiation is being emitted from the optical fiber to activate the chemical in close proximity to the endolumenal wall. This method can be modified or repeated as desired to achieve a coating of desired character and thickness. The exact chemical make-up and characteristics of the coating material is not central to the present case, which is directed to apparatus and methods for applying coatings of various character to the endolumenal wall of a medical device, except that the coating material must have a component that reacts to the radiation carried by the optical fiber.

The previously described method and apparatus, and the attributes and characteristics of same, will be better understood from the following detailed description, when read in conjunction with the accompanying drawings, wherein like reference characters refer to like parts throughout the several views and different embodiments of the present invention.

DESCRIPTION OF THE PREFERRED EMBODIMENTS

Figure 1:
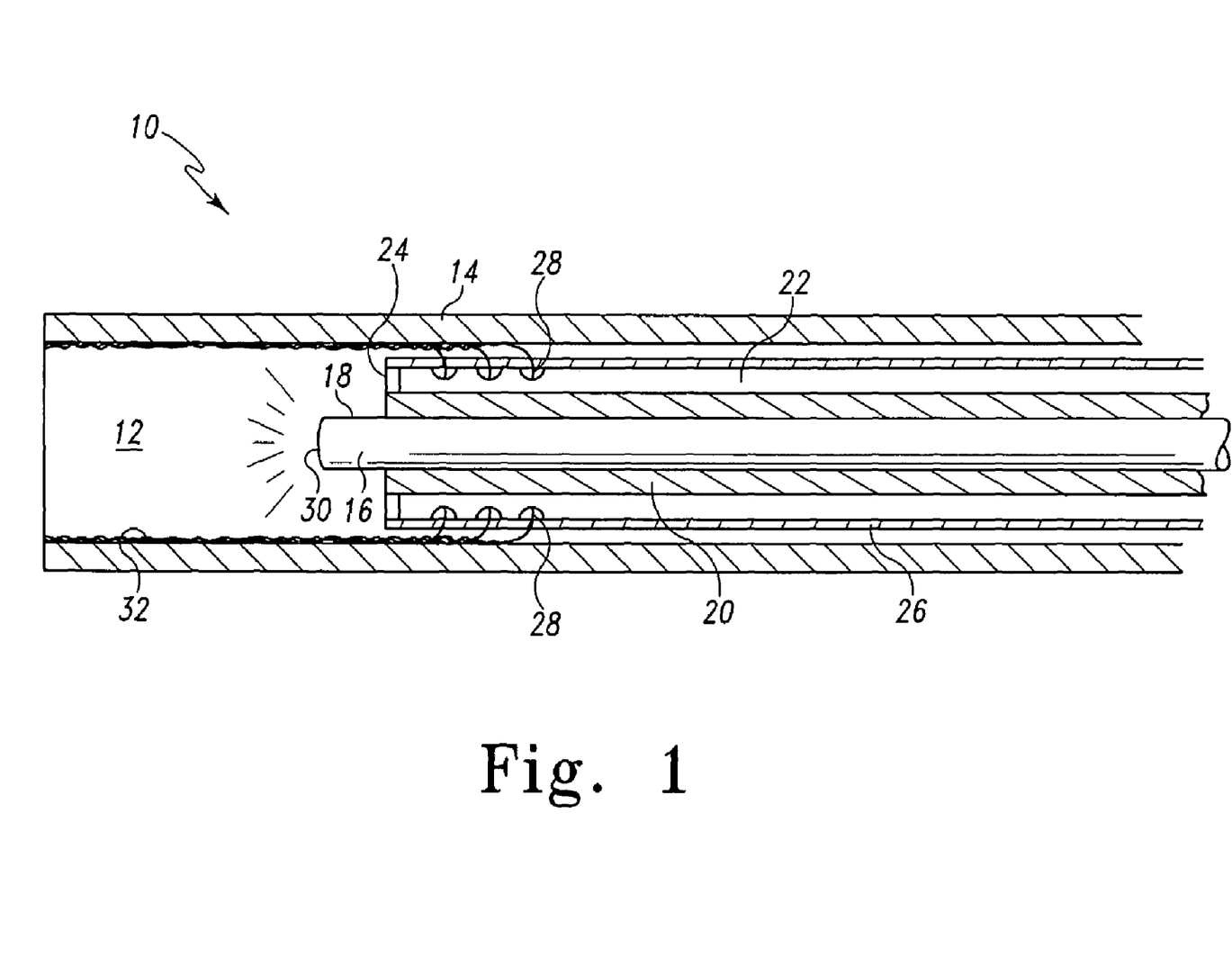
FIG. 1 is a cross-sectional view of a first embodiment of a distal end of an apparatus of the present invention.

Apparatus 10 for applying a coating to an endolumenal wall 12 of a medical device 14 is shown in FIG. 1. The medical device 14 can be, for example, a catheter, introducer, needle, stent frame or stent graft. The apparatus 10 includes an optical fiber 16 having a distal end 18. The optical fiber 16 is surrounded by an opaque wall 20. The opaque wall 20 can be further surrounded by a fluid-carrying channel 22 having a distal end 24. An outer wall 26 can surround the fluid-carrying channel 22. A plurality of openings 28 can be provided in the outer wall 26 adjacent to the distal end 24 of the fluid-carrying channel 22. The outer wall 26 can also be opaque to radiation having a suitable wavelength to interact with a chemical agent of the coating material to be applied to the endolumenal wall. The distal end 18 of the optical fiber 16 is configured to disperse any radiation traveling down the optical fiber 16 onto the endolumenal wall 12 of the medical device 14. The optical fiber 16 must be capable of carrying radiation having a suitable wavelength to interact with a chemical agent of the coating material to be applied to the endolumenal wall 12. The configuration of the distal end 18 can be a simple divergent lens shape 30 that will disperse the light in a well known manner to interact with any fluid 32 that may be dispensed onto the endolumenal wall 12 through the openings 28.

The fluid 32 can include lubricious hydrophilic polymers, such as, for example, a polysiliane or a polyfluoroethylene selected to provide various frictional characteristics. The fluid 32 can also include, for example, a therapeutic substance such as actinomycin D, paclitaxel, docetaxel, or rapamycin. The fluid 32 can also include, for example a solvent such as, for example, water, alcohol or ether. The fluid 32 can also include, for example, therapeutic substances can also be antineoplastic agents, antiproliferative agents, anti-inflammatory agents, growth control factors, antibiotics, antioxidants, and combinations thereof. The fluid 32 must have a component that reacts to the radiation from the distal end 18 of the optical fiber 16. Suitable radiation reactive components include, for example, anthraquinone, benzophenone, thioxanthone, and acetophenone.

Figure 2:
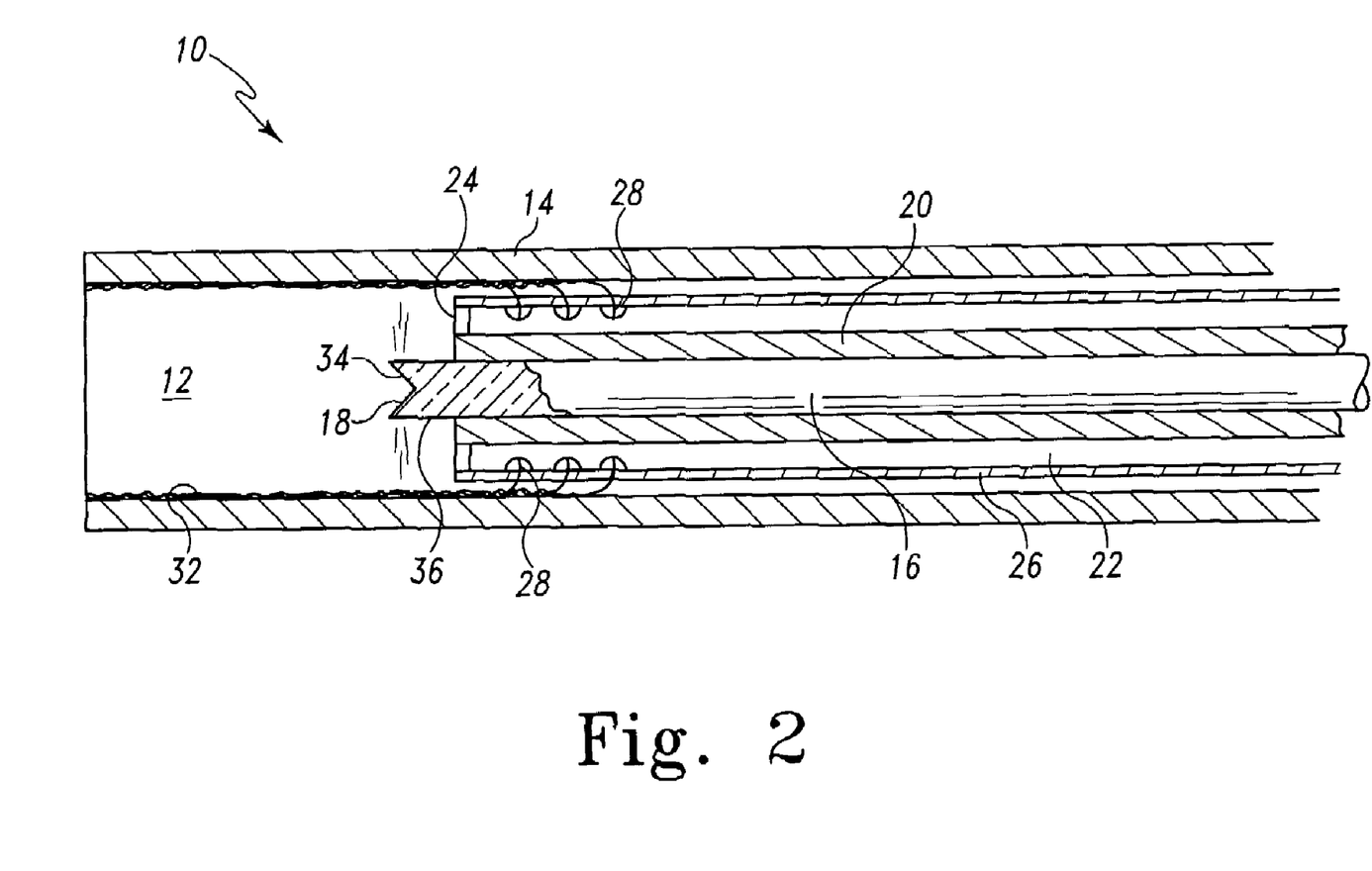
FIG. 2 is a cross-sectional view of a second embodiment of a distal end of an apparatus of the present invention.

An alternative structure for the apparatus 10 is shown in FIG. 2 wherein the distal end 18 of the optical fiber 16 can include an inwardly protruding conical surface 34. The conical surface 34 can be formed to reflect any radiation traveling down the optical fiber so that the radiation is directed radially outward through side wall 36 to interact with any fluid 32 that may be dispensed onto the endolumenal wall 12 through the openings 28. The openings 28 can be spaced around the outer wall 26 in any pattern that will permit at least a monomolecular film of the fluid 32 to be dispensed onto the endolumenal wall 12. When the wall 12 of the medical device 14 is continuous, the thickness of the film of fluid 32 can be controlled by providing a flow a gas between the outer wall 26 and the endolumenal wall 12. The flow of gas between the outer wall 26 and the endolumenal wall 12 can also act as a centering mechanism for the apparatus 10 within the medical device 14, which may contribute to a more uniform distribution of the fluid 32. The outer wall 26 of the apparatus 10 can be dimensioned to fit within, but be movable with respect to, the endolumenal wall 12 of the medical device 14. The outer wall 26 can be dimensioned to define a capillary space between the outer wall 26 and the endolumenal wall 12 to aid in the transport of the fluid 32 out of the channel 22 and onto the endolumenal wall 12.

Figure 3:
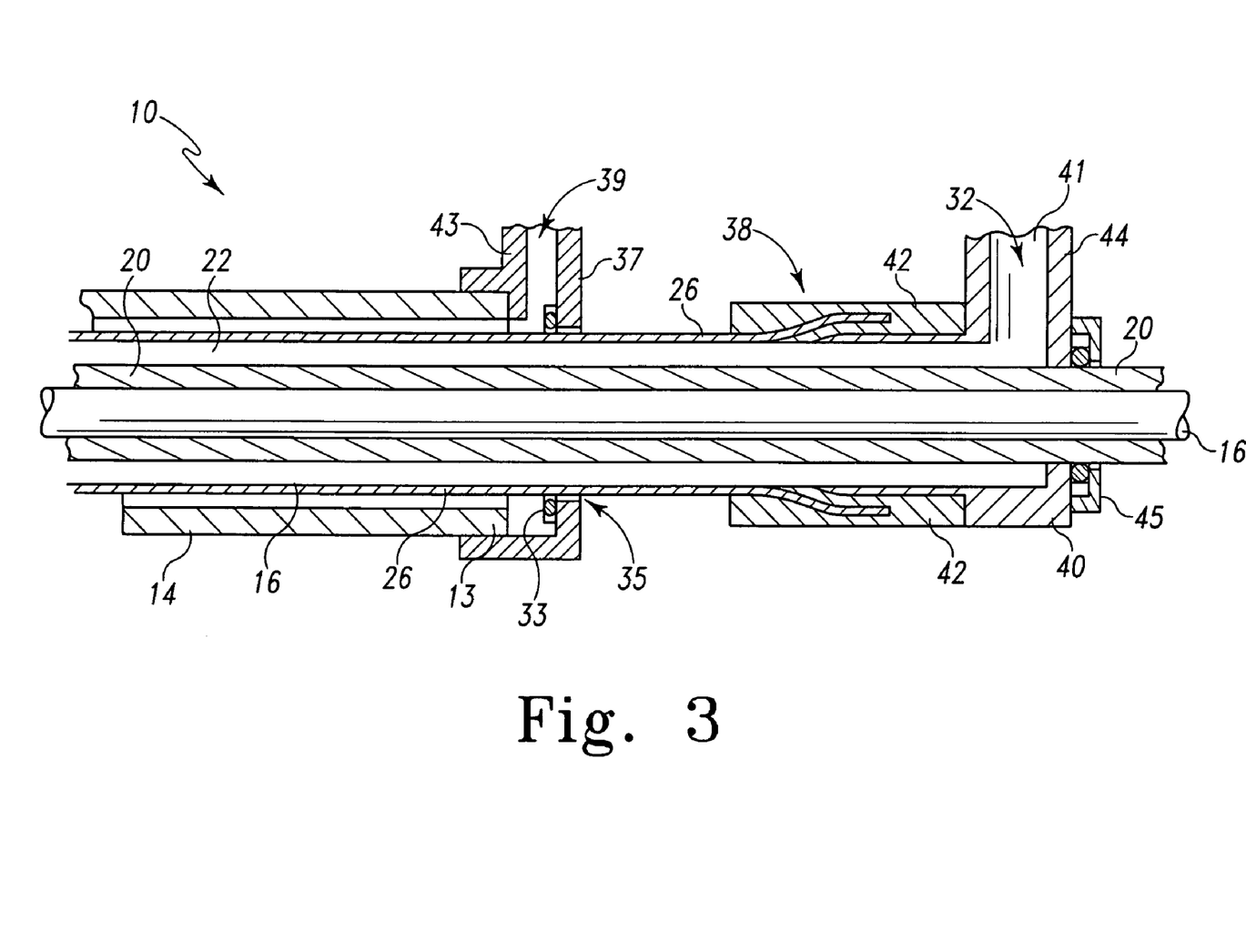
FIG. 3 is a cross-sectional view of a proximal end of an apparatus of the present invention.

The apparatus 10, of either FIG. 1 or FIG. 2, can also include a proximal end 38 as shown in FIG. 3. The proximal end 38 can include a liquid inlet bushing 40 that surrounds the optical fiber 16. A molded fitting 42 can couple the bushing 40 to the outer wall 26. The inlet bushing includes an opening 41 for receiving the fluid 32 from a source described below. The optical fiber 16 can pass through an end wall 44 of the bushing 40 toward a suitable source of radiation having a suitable wavelength to interact with a chemical agent of the coating material to be applied to the endolumenal wall. The bushing 40, including the end wall 44, can also be opaque to radiation having a suitable wavelength to interact with the reactive chemical agent of the coating material. The end wall 44 can be coupled to the opaque wall 20 with an O-ring or other seal 45 to prevent the fluid 32 from leaking from the bushing 40 around the opaque wall 20.

The apparatus 10 can include a plenum 43 that can be coupled to an end 13 of the medical device 14. The plenum 43 can include an inlet 39 coupled to a source of gas, which can be air or another gas such as, for example, nitrogen, that is pressurized sufficiently to cause a longitudinal flow of gas between the outer wall 26 and the endolumenal wall 12 of the medical device 14. The gas can be selected to have a vapor component that will contribute to the development of a uniform thickness of the film of fluid 32. The plenum 43 can include an end wall 37 having an opening 35 for receiving the optical fiber 16, opaque wall 20 and outer wall 26. A seal 33 can be provided between the opening 35 and outer wall 26 to prevent escape of the gas through the opening 35.

Figure 4:
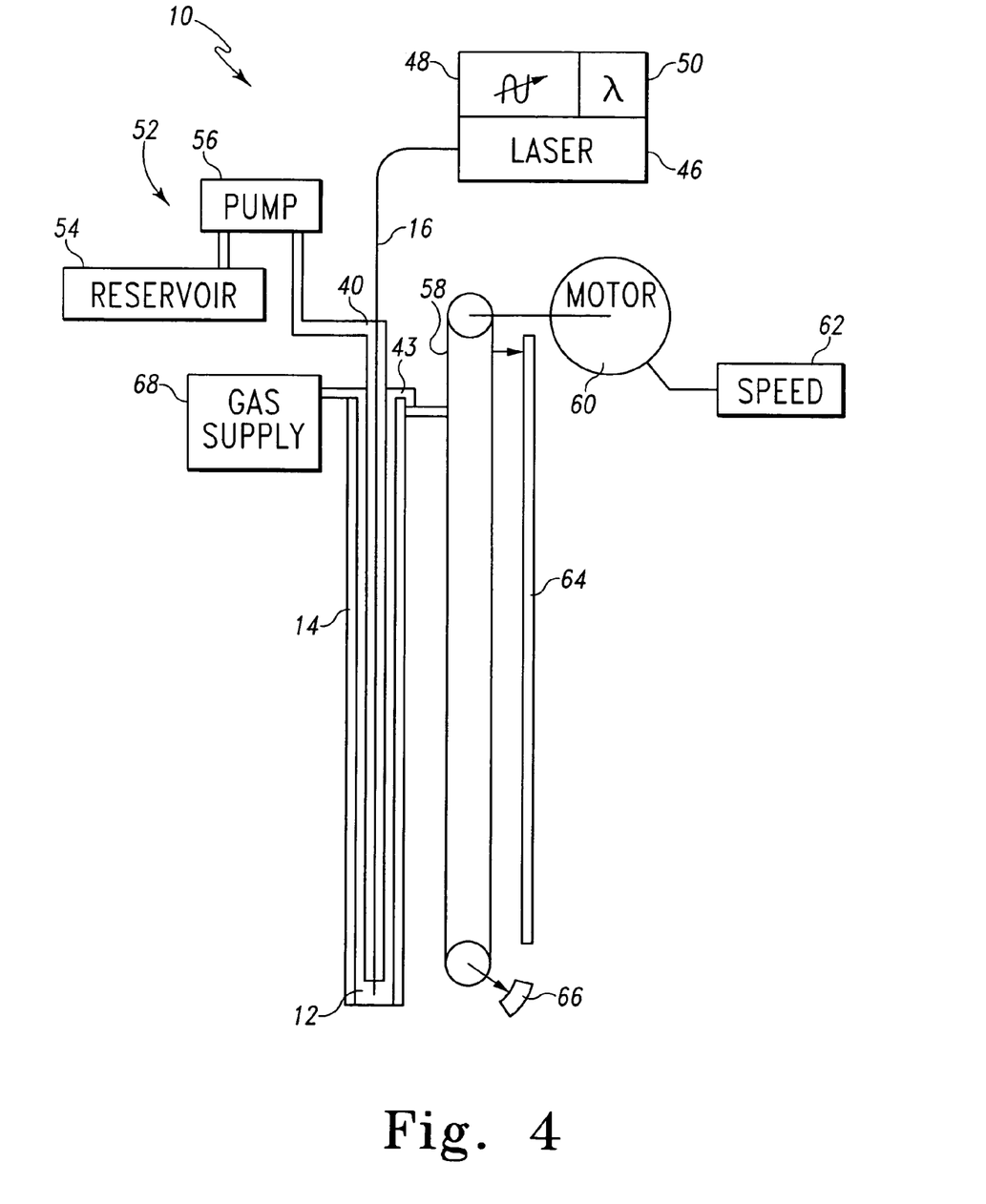
FIG. 4 is a block diagram of an apparatus of the present invention.

The apparatus 10 is schematically shown in FIG. 4 to include an optical fiber 16 coupled to a source 46 of radiation of a suitable wavelength to interact with the chemical agent of the coating material. The radiation source 46 can include an intensity control 48 to govern the amount of radiation to be delivered to the optical fiber. The radiation source 46 can also include a wavelength tuning or selection control 50 for selecting radiation of a suitable wavelength for interaction with the chemical agent of the coating material. The apparatus 10 can include a supply 52 of liquid containing a coating material to be applied to the endolumenal wall 12. The liquid supply 52 can include a reservoir 54 and a pump 56. The liquid supply 52 can be connected to the bushing 40 shown in FIG. 3. A gas supply 68 can supply a flow of a gas to the plenum 43 in sufficient quantity to cause a flow of gas longitudinally between the endolumenal wall 12 and the optical fiber 16. The apparatus 10 can also include a traction device 58 for causing longitudinal movement between the optical fiber 16 and the endolumenal wall 12 of the medical device 14. The traction device 58 can be coupled to or include a motor 60 with a speed control 62 for regulating the rate of relative movement between the optical fiber 16 and the medical device 14. The traction device 58 can also be coupled to a position sensor 64, a drag sensor 66, and other controls for sensing and governing the rate of movement, application of the liquid, and application of radiation.

Using an apparatus like those disclosed in the preceding figures, a coating can be applied to an endolumenal wall of a medical device in a variety of related processes that can include the steps of positioning an optical fiber with a distal end within the lumen, providing a photo-activated chemical in contact with the endolumenal wall adjacent to the optical fiber distal end, supplying the optical fiber with radiant energy of a wavelength selected to interact with the photo-activated chemical, and moving the optical fiber with respect to the lumen at a controlled rate during the photo activation. The process steps can be repeated as often as necessary to deposit the desired amount of photo-activated chemicals on the endolumenal wall. The process steps can be practiced over the entire length of a selected device or limited to only selected regions within the lumen.

The foregoing detailed description should be regarded as illustrative rather than limiting, and the following claims, including all equivalents, are intended to define the spirit and scope of this invention.

The invention claimed is:

1. A method of coating an endolumenal wall of a lumen of a previously manufactured medical device comprising the steps of:
    positioning a distal end of an optical fiber within the lumen of the previously manufactured medical device,
    surrounding the optical fiber with a fluid-carrying channel having an outer wall with a distal opening adjacent the optical fiber distal end,
    providing a photo-activated chemical within the fluid-carrying channel to be dispensed onto the endolumenal wall of the lumen,
    coupling the optical fiber to a source of radiation that can be carried by the optical fiber to the distal end of the optical fiber, the radiation being capable of activating the chemical within the lumen, and
    withdrawing the optical fiber and fluid-carrying channel simultaneously from the lumen at a controlled rate while the radiation is being emitted from the optical fiber distal end to activate the chemical in close proximity to the endolumenal wall.

2. The method of claim 1, wherein the providing step comprises the steps of
    coupling the fluid-carrying channel to a supply of the photo-activated chemical, and
    pumping the photo-activated chemical from the supply through the fluid-carrying channel and to the distal opening.

3. The method of claim 1 wherein the positioning step includes the step of leaving a capillary space between the endolumenal wall and the outer wall of the fluid-carrying channel.

4. The method of claims 1 or 3, wherein the providing step comprises the step of supplying a flow of gas between the outer wall of the fluid-carrying channel and the endolumenal wall of the lumen.

5. The method of claim 1, further comprising:
    inhibiting any pre-mature exposure of the photo-activated chemical by positioning an opaque wall between the optical fiber and the fluid-carrying channel.

6. The method of claim 1, further comprising:
    repeating the steps of claim 2 to deposit the desired amount of photo-activated chemicals on the endolumenal wall.

7. The method of claim 1, further comprising:
    limiting the emission of radiation from the optical fiber to only selected portions for the endolumenal wall.

8. A method of coating an endolumenal wall of a lumen of a previously manufactured medical device comprising the steps of:
    positioning a distal end of an optical fiber within the lumen of said previously manufactured medical device, the optical fiber coupled a source of radiation that can be carried by the optical fiber to the distal end of the optical fiber,
    surrounding the optical fiber with a fluid-carrying channel within the lumen of said previously manufactured medical device, the fluid-carrying channel having an outer wall with a distal end and having an aperture receiving the optical fiber, the fluid-carrying channel including at least one opening through the outer wall, the at least one opening in communication with the lumen and the fluid-carrying channel, the distal end of the optical fiber extending past the opening,
    providing a photo-activated chemical within the fluid-carrying channel to be dispensed onto the endolumenal wall of the lumen through the at least one opening,
    emitting radiation from the optical fiber distal end, the radiation configured to activate the chemical in close proximity to the endolumenal wall, and
    withdrawing the optical fiber and fluid-carrying channel simultaneously from the lumen of said previously manufactured medical device at a controlled rate during the emitting step.

9. The method of claim 8, wherein the at least one opening includes a plurality of openings spaced around the outer wall, wherein the spacing between the openings is configured to permit the formation of a monomolecular film of the photo-activated chemical along the endolumenal wall.

10. The method of claims 9, wherein the providing step comprises the step of supplying a flow of gas between the outer wall of the fluid-carrying channel and the endolumenal wall of the lumen to control the thickness of said film.

11. The method of claims 8, wherein the providing step comprises the step of supplying a flow of gas between the outer wall of the fluid-carrying channel and the endolumenal wall of the lumen to center the fluid-carrying channel within the lumen.

12. The method of claim 8, wherein the positioning step includes the step of leaving a space between the endolumenal wall and the outer wall of the fluid-carrying channel, said space configured to permit the transport of the photo-activated chemical out of the fluid-carrying channel and onto the endolumenal wall through capillary action.

13. The method of claim 8, wherein the providing step comprises the steps of
coupling the fluid-carrying channel to a supply of the photo-activated chemical, and
pumping the photo-activated chemical from the supply through the fluid-carrying channel to the at least one opening.

14. The method of claim 8, further comprising:
inhibiting any pre-mature exposure of the photo-activated chemical by positioning an opaque wall between the optical fiber and the fluid-carrying channel.

15. The method of claim 8, further comprising:
limiting the emission of radiation from the optical fiber to only selected portions for the endolumenal wall.

16. The method of claim 8, wherein the aperture extends through the fluid-carrying channel, the aperture having an opaque wall facing the optical fiber to inhibit any pre-mature exposure of the photo-activated chemical.

17. The method of claim 8, wherein the outer wall has a surface facing the endolumenal wall, said surface being opaque to enhance the bonding of the photo-activated chemical to the endolumenal wall.

18. The method of claim 8, further comprising the step of coupling the fluid-carrying channel and the optical fiber.

19. The method of claim 8, wherein the withdrawing step includes withdrawing the optical fiber and fluid-carrying channel simultaneously from the lumen of said previously manufactured medical device at the controlled rate during the emitting step and the providing step.

* * * * *

UNITED STATES PATENT AND TRADEMARK OFFICE
CERTIFICATE OF CORRECTION

PATENT NO. : 7,604,830 B2
APPLICATION NO. : 11/159707
DATED : October 20, 2009
INVENTOR(S) : Brian C. Case and Darin G. Schaeffer Page 1 of 1

It is certified that error appears in the above-identified patent and that said Letters Patent is hereby corrected as shown below:

In the Claims

In column 6, line 14, please delete "2" and insert in lieu thereof --1--.

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,604,830 B2  Page 1 of 1
APPLICATION NO. : 11/159707
DATED : October 20, 2009
INVENTOR(S) : Case et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 963 days.

Signed and Sealed this

Fifth Day of October, 2010

David J. Kappos
*Director of the United States Patent and Trademark Office*